US00PP33258P2

(12) United States Plant Patent
Pineau

(10) Patent No.: US PP33,258 P2
(45) Date of Patent: Jul. 13, 2021

(54) ***HIBISCUS* PLANT NAMED 'MINSYROU17'**

(50) Latin Name: *Hibiscus syriacus*
Varietal Denomination: MINSYROU17

(71) Applicant: Hortival Diffusion SAS, Beaufort en Valee (FR)

(72) Inventor: Patrick Pineau, Saint Mathurin sur Loire (FR)

(73) Assignee: Hortival Diffusion SAS

( * ) Notice: Subject to any disclaimer, the term of this patent is extended or adjusted under 35 U.S.C. 154(b) by 0 days.

(21) Appl. No.: 17/038,828

(22) Filed: Sep. 30, 2020

(51) Int. Cl.
*A01H 5/02* (2018.01)
*A01H 6/60* (2018.01)

(52) U.S. Cl.
USPC ..... Plt./257
CPC ..... *A01H 6/608* (2018.05)

(58) Field of Classification Search
USPC ..... Plt./257
CPC ..... A01H 5/02
See application file for complete search history.

(56) References Cited

U.S. PATENT DOCUMENTS

PP31,305 P2 * 12/2019 Pineau ..... A01H 6/608 Plt./257

OTHER PUBLICATIONS

PLUTO UPOVROM Plant Variety Database Citation for 'MINSYROU17' as per QZ PBR 20192007; Dec. 16, 2019; 1 page. (Year: 2019).*

* cited by examiner

*Primary Examiner* — Kent L Bell
(74) *Attorney, Agent, or Firm* — Cassandra Bright

(57) ABSTRACT

A new and distinct *Hibiscus* cultivar named 'MINSYROU17' is disclosed, characterized by large, single, magenta flowers with a small darker eye. Plants are well-branched, upright, and compact. The new variety is a *Hibiscus*, normally produced as an outdoor garden or container plant.

2 Drawing Sheets

Figure 1:
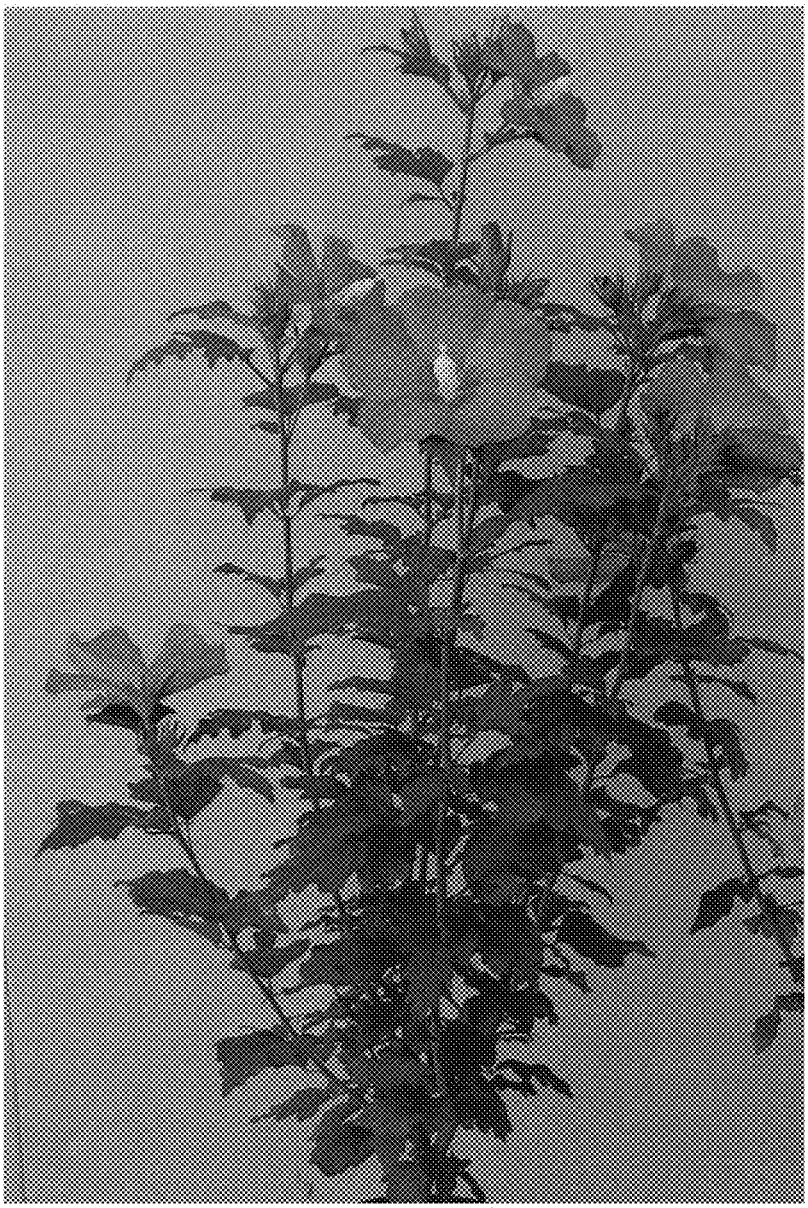

Latin name of the genus and species: *Hibiscus syriacus*. Variety denomination: 'MINSYROU17'.

BACKGROUND OF THE INVENTION

The new *Hibiscus* cultivar is a product of a planned breeding program conducted by the inventor, Patrick Pineau. The objective of the breeding program was to produce vigorous *Hibiscus syriacus* cultivars with healthy foliage. The cross resulting in this new variety was made during 2011.

The seed parent is the unpatented *Hibiscus syriacus* 'Mineru'. The pollen parent is the unpatented variety *Hibiscus syriacus* 'Rubis'. The new variety was identified and selected as a potentially interesting selection in October 2014. Selection was made at a commercial nursery in La Menitre, France.

Asexual reproduction of the new cultivar 'MINSYROU17' was first performed in February 2015 in La Menitre, Maine Et Loire, France, by cleft grafting. Subsequent propagation has shown that the unique features of this cultivar are stable and reproduced true to type in 5 successive generations. Date of first sale was Oct. 1, 2019, occurring in France. This sale was made directly by the inventor or one who obtained the claimed invention directly or indirectly from the inventor. This sale and all public disclosures made between Oct. 1, 2019 and the filing of this application fall within the exception allowed under 102(b)(1).

SUMMARY OF THE INVENTION

The cultivar 'MINSYROU17' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'MINSYROU17'. These characteristics in combination distinguish 'MINSYROU17' as a new and distinct *Hibiscus* cultivar:

1. Magenta flowers with a small darker eye.
2. Large single flowers.
3. Moderate to vigorous.
4. Well branched.

PARENT COMPARISON

Plants of the new cultivar 'MINSYROU17' are similar to plants of the seed parent in most horticultural characteristics, however, plants of the new cultivar 'MINSYROU17' differ in the following:

1. 'MINSYROU17' has single flowers, the seed parent has semi-double flowers.
2. 'MINSYROU17' has a magenta flower color with a small darker eye, the seed parent has a lavender-magenta flower color.
3. 'MINSYROU17' has regularly shaped petals, the seed parent has irregularly shaped petals.

Plants of the new cultivar 'MINSYROU17' are similar to plants of the pollen parent in most horticultural characteristics, however, plants of the new cultivar 'MINSYROU17' differ in the following;

1. 'MINSYROU17' is more vigorous with more branches than pollen parent.
2. 'MINSYROU17' has larger flowers than the pollen parent.
3. Petals of 'MINSYROU17' are overlapping, petals of the pollen parent do not overlap as much.
4. 'MINSYROU17' has a magenta flower color with a small darker eye, the pollen parent has a lavender-magenta flower color.

COMMERCIAL COMPARISON

Plants of the new cultivar 'MINSYROU17' can be compared to the variety *Hibiscus* 'SHIMRR38', U.S. Plant Pat. No. 27,195. These varieties are similar in most horticultural characteristics however, 'MINSYROU17' differs in the following:

1. 'MINSYROU17' has larger flowers than 'SHIMIRR38'.
2. 'MINSYROU17' has broader leaves than 'SHIMIRR38'.

BRIEF DESCRIPTION OF THE PHOTOGRAPHS

The accompanying photograph in FIG. 1 illustrates in full color a typical plant of 'MINSYROU17' grown in a 2-gallon pot at approximately 2 years old in Grand Haven, Mich.

Figure 2:
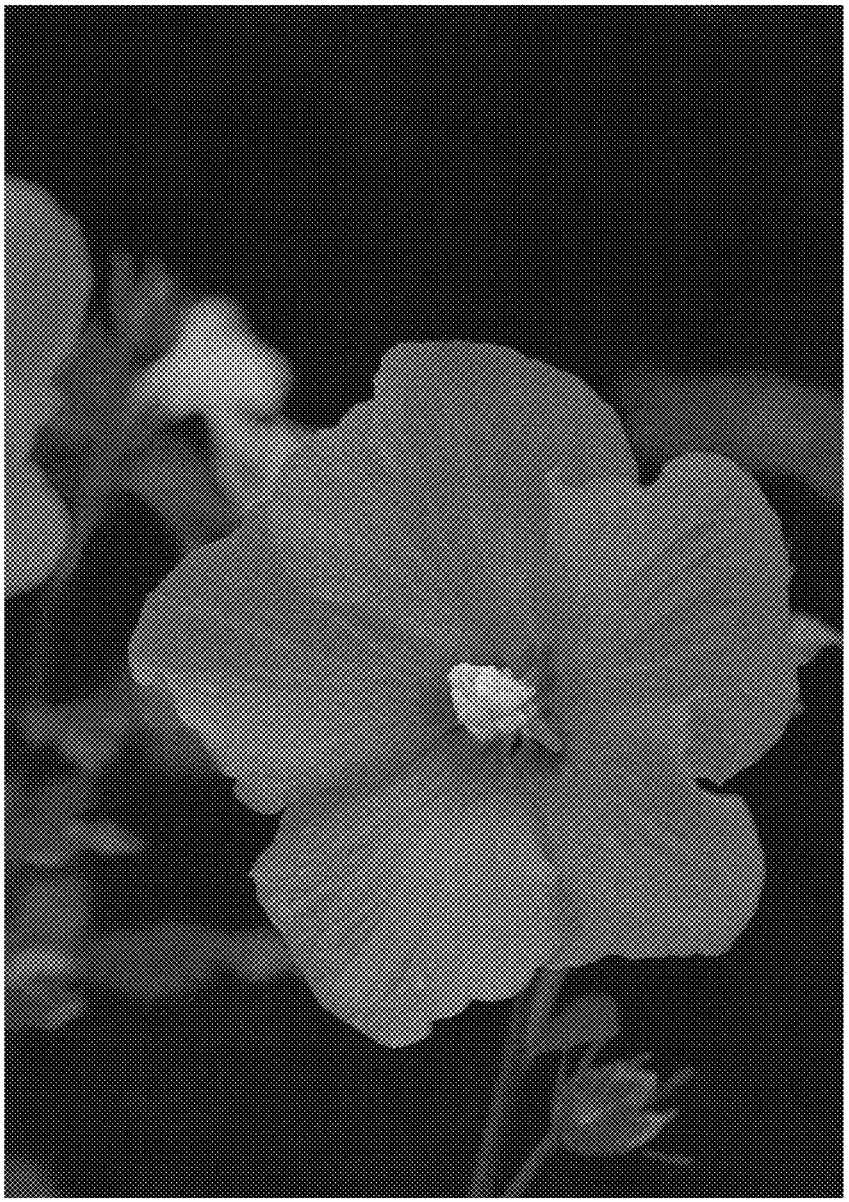

FIG. 2 illustrates in full color a typical flower of 'MINSYROU17'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, $6^{th}$ edition, except where general terms of ordinary dictionary significance are used. The following observations and measurements describe 'MINSYROU17' plants grown in an unheated polyhouse in Grand Haven, Mich. under natural lighting. Measurements were taken during the August of 2020. The plants were about 2 years old in 3-gallon containers. The growing temperature ranged from approximately −5° C. to 27° C. Measurements and numerical values represent averages of typical plant types.

Botanical classification: *Hibiscus syriacus* 'MINSYROU17'.

PROPAGATION

Time to initiate roots: 20 days at approximately 18° C. to 27° C.

Root description: Fibrous, medium root thickness. Tan/brown in color, not effectively measured with a color chart.

Time to produce a rooted young plant: About 90 days at approximately 18° C. to 27° C.

PLANT

Plant type: Perennial, hardy deciduous flowering shrub.
Age of plant described: Approximately 2 years old.
Growth habit: Upright and compact.
Height: 83 cm.
Spread: 49 cm.
Branching characteristics: Well branched.
Length of primary lateral branches: 48 cm.
Quantity of lateral branches: About 10.
Characteristics of primary lateral branches:
- *Diameter.*—6 to 10 mm.
- *Color.*—New growth near Green 143A, mature growth near Yellow-Green 146A.
- *Texture.*—New growth pubescent.

Internode length: 3 to 7 cm.

FOLIAGE

Leaf:
- *Arrangement.*—Alternate.
- *Quantity.*—Approximately 20 per branch.
- *Average length.*—7 cm.
- *Average width.*—6 cm.
- *Shape of blade.*—Obvate, 3-lobed.
- *Apex.*—Acute.
- *Base.*—Obtuse.
- *Margin.*—Lobed, crenate.
- *Texture of top surface.*—Slightly rough, ribbed.
- *Texture of bottom surface.*—Rough, with distinct veins.
- *Color.*—Young foliage upper side: RHS Green 137A. Young foliage under side: RHS Yellow-Green 147B. Mature foliage upper side: RHS Green NN137A. Mature foliage under side: RHS Green NN137C.
- *Venation.*—Type: Pinnate. Venation color upper side: RHS Green NN137A. Venation color under side: RHS Green NN137C.
- *Petiole.*—Length: 3.5 cm. Diameter: 2 mm. Color: RHS Green NN137B. Texture: Upper surface pubescent, lower surface glabrous.

FLOWER

Natural flowering season: Summer.
Flower type and habit: Solitary, rotate.
- *Single, double, multiplex.*—Single.
- *Petals overlapping.*—Moderately overlapping.

Rate of flower opening: 1 to 2 days from bud to fully opened flower.
Flower longevity on plant: 1 to 2 days.
Persistent or self-cleaning: Self-cleaning.
Bud:
- *Shape.*—Ovate.
- *Length.*—3.5 cm.
- *Diameter.*—1.5 cm.
- *Color.*—RHS Red-Purple 59A.

Flower size:
- *Diameter.*—9.5 cm.
- *Depth.*—5 cm.

Petals:
- *Quantity.*—5.
- *Arrangement.*—Whorled, overlapping.
- *Length.*—6.5 cm.
- *Width.*—5.0 cm.
- *Shape.*—Obovate.
- *Apex.*—Obtuse.
- *Base.*—Attenuate.
- *Margin.*—Entire, slight undulation.
- *Texture, upper and lower surfaces.*—Smooth.
- *Color.*—When opening, upper surface: RHS Greyed-Purple 186C with a small Greyed-Purple 185A eye. When opening, lower surface: RHS Greyed-Purple 185D, base fading to White NN155D. Faint, small Greyed-Purple 185A eye. Fully opened, upper surface: RHS Greyed-Purple 186C with a small Greyed-Purple 185A eye. Fully opened, lower surface: RHS Greyed-Purple 185D, base fading to White NN155D. Faint, small Greyed-Purple 185A eye. Ratio of basal blotch/eye to petal size: About 15% of petal blade blotched. Feathering color: RHS Greyed-Purple 185A Feathering size: Minimal, about 5 to 10 mm.

Sepals:
- *Quantity.*—5.
- *Length.*—2.5 cm.
- *Width.*—2 mm.
- *Shape.*—Narrow deltate.
- *Margin.*—Entire.
- *Color.*—RHS Green 143C upper surface, 143D lower surface.
- *Texture.*—Glabrous all surfaces.

Peduncles:
- *Length.*—2.25 cm.
- *Diameter.*—3 mm.
- *Angle.*—About 45° to the lateral branch.
- *Strength.*—Strong.
- *Texture.*—Pubescent.
- *Color.*—RHS Green 143B.

Fragrance: None.

REPRODUCTIVE ORGANS

Stamens:
- *Number.*—50.

Anthers:
- *Shape.*—Irregular sphere.
- *Length.*—About 2 mm.
- *Color.*—Near RHS White 155A.
- *Pollen color.*—Near RHS White 155A.
- *Pollen amount.*—Moderate.

Pistil:
- *Number.*—1.
- *Length.*—4.25 cm.
- *Style.*—Length: 3.7 cm. Color: Near RHS White 155C.
- *Stigma.*—Shape: Peltate. Color: Near RHS White 155C.
- *Ovary color.*—Near RHS White 155C with light shading of Red-Purple 60B.

OTHER CHARACTERISTICS

Seeds: Capsule, typically about 1 cm in diameter and length. Pubescent, colored near Grey-Brown 199B. Moderately abundant lightly pubescent seed.

Disease/pest resistance: Improved resistance to *Sclerotinia*. No other resistance nor susceptibility to normal diseases and pests of *Hibiscus syriacus* have been observed.

Temperature tolerance: Low temperature tolerance to at least USDA zone 4, high temperature tolerance to at least 40° C.

What is claimed is:

1. A new and distinct cultivar of *Hibiscus* plant named 'MINSYROU17' as herein illustrated and described.

* * * * *